US006348312B1

(12) United States Patent
Peyman et al.

(10) Patent No.: US 6,348,312 B1
(45) Date of Patent: Feb. 19, 2002

(54) STABILIZED OLIGONUCLEOTIDES AND THEIR USE

(75) Inventors: Anuschirwan Peyman, Kelkheim; Eugen Uhlmann, Glashütten; Matthias Mag, Oberursel; Gerhard Kretzschmar, Eschborn; Matthias Helsberg, Kelkheim; Irvin Winkler, Liederbach, all of (DE)

(73) Assignee: Hoescht Aktiengesellschaft (DE)

( * ) Notice: Subject to any disclaimer, the term of this patent is extended or adjusted under 35 U.S.C. 154(b) by 0 days.

(21) Appl. No.: 08/337,120

(22) Filed: Nov. 10, 1994

(30) Foreign Application Priority Data

Nov. 12, 1993 (DE) .......................................... 43 38 704

(51) Int. Cl.$^7$ ................................................. C12Q 1/60
(52) U.S. Cl. ......................... 435/6; 536/22.1; 536/23.1; 536/25.3; 514/44
(58) Field of Search ............................. 536/22.1, 23.1, 536/25.3; 514/44, 45; 435/6

(56) References Cited

FOREIGN PATENT DOCUMENTS

| EP | 0300687 | * | 1/1989 |
|---|---|---|---|
| EP | A-0552766 | | 7/1993 |
| WO | 87/07300 | | 12/1987 |
| WO | 88/07544 | | 10/1988 |
| WO | 8807544 | * | 10/1988 |
| WO | 89/08146 | | 9/1989 |
| WO | 92/03139 | | 3/1992 |
| WO | 92/20348 | | 11/1992 |
| WO | 92/20697 | | 11/1992 |
| WO | 93/01286 | | 1/1993 |
| WO | 93/17125 | | 9/1993 |
| WO | 94/01551 | | 1/1994 |
| WO | 94/02499 | | 2/1994 |
| WO | 94/26888 | | 11/1994 |
| WO | 95/01363 | | 1/1995 |

OTHER PUBLICATIONS

Kurokawa et al, Nucleic Acids Res. 16: 5201 (1988).*
Kim et al, Am. J. Physiol. 264(1)(Part 1 of Two), F66 (1993).*
Tamkun et al., Cell 46: 271 (1986).*
Staunton et al, Cell 52: 925 (1988).*
Th'ng et al, Cell 63: 313 (1990).*
Matsumoto et al., EMBO J. 6: 637 (1987).*
Shimatsu et al, J. Biol. Chem. 262: 7894 (1987).*
Sommer et al, Biochem. Biophys. Res. Commun. 144: 543 (1987).*
Smith et al, J. Virol. 64: 6286 (1990).*
Robert–Guroff et al, J. Virol. 64: 3391 (1990).*
Mackem et al, J. Virol. 44: 939 (1982).*
Minor et al, J. gen. Virol. 69: 1091 (1988).*
Hayday et al, Nature 307: 334 (1984).*
Calabi et al, EMBO J. 4: 667 (1985).*
Majello et al, Proc. Natl. Acad. Sci. USA 83: 9636 (1986).*
Van Bevern et al, Cell 32: 1241 (1983).*
Ullrich et al, Nature 309: 418 (1984).*
Petch et al, Mol. Cell. Biol. 10: 2973 (1990).*
Bienz–Tadmor et al, EMBO J. 4: 3209 (1985).*
Jenkins et al, Nucleic Acids Res. 12: 5609 (1984).*
Simmons et al, Nature 331: 624 (1988).*
Bender et al, Proc Natl. Acad. Sci. USA 83: 3204 (1986).*
Derwent Abstract of German Priority document DE 4321946 as claimed in WOA–95/01363.
Lisziewicz et al., "Long–term Treatment of Human Immunodeficiency Virus—infected Cells with Antisense Oligonucleotide Phosphorothiates", P.N.A.S. USA, 90: p. 3860 only (1993).
Chemical Abstracts, 114(7):55778n (1991), McGrath, "Tumor–specific Antisense Oligonucleotides for Controlling Cancer".
E. Uhlmann et al., "Antisense Oligonucleotides: A New Therapeutic Principle," Chemical Reviews, 90(4):544–583 (1990).
J. Milligan et al., "Current Concepts in Antisense Drug Design," Journal of Medicinal Chemistry, 36(14):1923–1937, (1993).
C. Stein et al., "Antisense Oligonucleotides as Therapeutic Agents—Is the Bullet Really Magical?", Science, 261:1004–1012, (1993).
S. Crooke et al., "Antisense Research and Applications, Medicinal Chemistry Strategies for Antisense Research," pp. 153–154 and 307–316, CRC Press, Inc., (1993).
P. Cook, "Medicinal Chemistry Strategies for Antisense Research," 9:149–187, CRC Press, Inc., (1993).
C. Stein et al., "Physiochemical Properties of Phosphorothioate Oligodeoxynucleotides," Nucleic Acids Research, 16(8), (1988).
T. Woolf et al., "The Stability, Toxicity and Effectiveness of Unmodified and Phosphorothioate Antisense Oligodeoxynucleotides in Xenopus Oocytes and Embryos," Nucleic Acids Research, 18(7):1763–1769, (1990).
M. Ghosh et al., "Phosphorothioate–Phosphodiester Oligonucleotide Co–Polymers: Assessment for Antisense Application," Anti–Cancer Drug Design, 8:15–32, (1993).
P. Furdon et al., "RNase H Cleavage of RNA Hybridized to Oligonucleotides Containing Methylphosphonate, Phosphorothioate and Phosphodiester Bonds," Nucleic Acids Research, 17(22), (1989).

(List continued on next page.)

*Primary Examiner*—James Martinell
(74) *Attorney, Agent, or Firm*—Finnegan, Henderson, Farabow, Garrett & Dunner, L.L.P.

(57) ABSTRACT

The invention relates to novel stabilized oligonucleotides in which at least one non-terminal pyrimidine nucleoside is modified, and to their use as a diagnostic or pharmaceutical for the treatment of viral infections, cancer or diseases in which integrins or cell-cell adhesion receptors are active.

67 Claims, No Drawings

OTHER PUBLICATIONS

C. Marcus–Sekura et al., "Comparative Inhibition of Chloramphenicol Acetyltransferase Gene Expression by Antisense Oligonucletide Analogues Having Alkyl Phosphotriester, Methylphosphonate and Phosphorothioate Linkages," Nucleic Acids Research, 15(14):5749–5763, (1987).

J.P. Shaw et al. "Modified Deoxyoligonucleotides Stable to Exonuclease Degradation in Serum," Nucleic Acids Research, 19(4):747–750, (1991).

H. Seliger et al., "Oligonucleotide Analogues with Terminal 3'–3'–and 5'–5'–Internucleotidic Linkages as Antisense Inhibitors of Viral Gene Expression," Nucleosides & Nucleotides, 10(1–3):469–477 (1991).

R. Giles et al., "Chimeric Oligodeoxynucleotide Analogues: Enhanced Cell Uptake of Structures Which Direct Ribonuclease H with High Specificity," Anti–Cancer Drug Design, 8:33–51, (1993).

G. Hoke et al, "Effects of Phosphorothioate Capping on Antisense Oligo–Nucleotide Stability, Hybridization and Antiviral Efficacy Versus Herpes Simples Virus Infection," Nucleic Acids Research, 19(20):5743–5748, (1991).

E. Uhlmann et al., "Chapter 16: Oligonucleotide Analogs Containing Dephospho–Internucleoside Linkages," Methods in Molecular Biology, 20:355–389, (1993).

E. Stirchak et al., "Uncharged Stereoregular Nucleic Acid Analogs: 2. Morpholino Nucleoside Oligomers with Carbamate Internucleoside Linkages," Nucleic Acids Research, 17(15):6129–6141, (1989).

B. Froehler et al., "Triple–Helix Formation by Oligodeoxynucleotides Containing the Carbocyclic Analogs of Thymidine and 5–Methyl–2'–Deoxy–cytidine," American Chemical Society, 114:8320–8322, (1992).

F. Vandendriessche et al., "Acylic Oligonucleotides: Possibilities and Limitations," Tetrahedron, 49(33):7223–7238, (1993).

M. Tarköy et al, "31. Nucleic–Acid Analogues with Constraint Conformational Flexibility in the Sugar–Phosphate Backbone ('Bicylo–DNA'), Part I, Preparation of (3'S, 5'R)–2'–Deoxy–3', –5'–ethano–$\alpha\beta$–D–Ribonucleosides ('Bicyclonucleosides')," Helvetica Chimica Acta, 76:481–511, (1993).

M. Manoharan, "Designer Antisense Oligonucleotides: Conjugation Chemistry and Functionality Placement," Antisense Research and Applications, 7:304–349, (1993).

M. Koga et al., "Alternating $\alpha,\beta$–Oligothymidylates with Alternating (3'$\rightarrow$3'– and (5'$\rightarrow$5')–Internucleotidic Phosphodiester Linkages as Models for Antisense Oligodeoxyribonucleotides," The Journal of Organic Chemistry, 56(12):3757–3759, (1991).

L. Bock et al, "Selection of Single–Stranded DNA Molecules that Bind and Inhibit Human Thrombin," Nature, 355:564–566, (1992).

D. Castanotta et al., "Biological and Functional Aspects of Catalytic RNAs," Critical Reviews in Eukaryotic Gene Expression, 2(4):331–357, (1992).

M. Sawadogo et al., "A Rapid Method for the Purification of Deprotected Oligodoxynucleotides," Nucleic Acids Research, 19(3):674, (1991).

J. Mann et al., "Synthesis and Properties of an Oligodeoxynucleotide Modified with a Pyrene Derivative at the 5'–Phosphate," Bioconjugate Chem., 3:554–558, (1992).

S. Biro et al., "Inhibitory Effects of Antisense Oligodeoxynucleotides Targeting c–myc mRNA on Smooth Muscle Cell Proliferation and Migration," Proc. Natl. Acad. Sci., 90:654–658, (1993).

* cited by examiner

STABILIZED OLIGONUCLEOTIDES AND THEIR USE

The invention relates to novel stabilized oligonucleotides in which at least one non-terminal pyrimidine nucleoside is modified, and to their use as a diagnostic or pharmaceutical for the treatment of viral infections, cancer or diseases in which integrins or cell-cell adhesion receptors are active.

Antisense oligonucleotides (AO) and triple-helix-forming oligonucleotides (TFO) have proved to be specific gene expression inhibitors in a large number of systems, both in vitro and in vivo [Uhlmann & Peyman, Chem. Rev. 1990, 90, 543; Milligan et al., J. Med. Chem. 1993, 36, 1923; Stein & Cheng, Science 1993, 261, 1004].

One of the main problems when using naturally occurring phosphodiesters (PO) oligonucleotides is their rapid degradation by a range of nucleolytic activities both in cells and in the cell culture medium. A range of chemical modifications was used to stabilize oligonucleotides. A review of the prior art is given, for example, by Milligan et al., supra, and Uhlmann & Peyman, supra. Stabilization against nucleolytic degradation can be effected by modifying or replacing the phosphate bridge, the sugar unit, the nucleic base, or by replacing the sugar-phosphate backbone of the oligonucleotides. Since the phosphate bridge is the center of nucleolytic attack, a large number of modifications of the internucleoside bridge were described, in particular. The most frequently used nuclease-resistant internucleoside bridges are phosphorothioate (PS), methylphosphonate (MeP) and phosphorodithioate (PA) bridges.

It must be borne in mind that the introduction of modifications alters not only the stability to nucleases, but simultaneously a large number of characteristics of the antisense oligonucleotides or triple-helix-forming oligonucleotides, such as, for example, their ability to enter cells, activation of RNase H, their specificity and their ability to hybridize with RNA (in the case of AO) or DNA (in the case of TFO) and the like. Moreover, there are indications that the stability of the serum, which is frequently used as a criterion for stability to nucleases, does not always reflect the intracellular activity [P. D. Cook in "Antisense Research and Applications", Crooke and Lebleu, Eds., CRC Press, Boca Raton, 1993, Chapter 9, pp. 149 et sec.]. This is why, in addition to the resistance to nucleases, the biological activity of antisense oligonucleotides or triple-helix-forming oligonucleotides gives information about the quality of such modifications.

As regards the question of the positions in the oligonucleotide at which such modifications are ideally to be effected, the following strategies have been developed [P. D. Cook (supra); Uhlmann & Peyman (supra); Milligan et al. (supra)]:

I) Exchange of All Internucleoside Bridges, for Example to Produce All-PS Oligonucleotides This exchange gives oligonucleotides which are extremely stable to nucleases. For example, degradation by endo-nucleases (S1 nucleases) and by endo/exo nuclease P1 in an all-PS oligonucleotide is slowed down by a factor of 2–45 relative to a PO oligonucleotide [Stein et al., Nucl. Acids Res. 1988, 16, 1763]. All-PS oligonucleotides are also resistant in intact cells. In Xenopus oocytes or embryos, the degradation of microinjected PO oligonucleotides proceeds with a half-life of 30 minutes, while all-PS oligonucleotides have a half-life of over three hours under the same conditions [Woolf et al., Nucl. Acids Res. 1990, 18, 1763]. All-MeP oligonucleotides are also extremely resistant to nucleases.

The disadvantage of all-PS, or all-MeP, oligonucleotides compared with the PO oligonucleotides is that their capability of forming stable hybrids with the target RNA is reduced. A further disadvantage of the all-PS oligonucleotides are the unspecific ("non-antisense") effects, which are frequently observed in this class of compounds [Milligan et al., supra; Stein & Cheng, supra].

Other uniformly modified derivatives for example all-2'-O-methyl-derivatives or all-α-2'-deoxyribo derivatives, are generally also characterized by having lost the capability of activating RNase H.

II) Copolymers of Modified and Unmodified Phosphodiester Bridges

Ghosh et al. [Anti-Cancer Drug Design 1993, 8, 15] describe a phosphorothioate-phosphodiester oligonucleotide containing various percentages of PS bridges. Their construction follows, for example, the pattern —(PS—PO—PO—PO)$_n$, (PS—PO—PO)$_n$, (PS—PO)$_n$, ((PO)$_2$—(PS)$_2$)$_n$, or (PO—PS—PS)$_n$. More specifically, Ghosh et al. disclose the following constructions: (PS—PO—PO—PO)$_n$ and ((PO)$_2$—(PS)$_2$)$_n$, wherein n=4, and (PS—PO)$_n$ and (PO—PS)$_n$ wherein n=8. They teach that a PS bridge content of at least 50% is required for selective translation inhibition and that the activity drops drastically when this content is less. The present invention shows that these results are incorrect and that a PS bond content of far less than 50% is sufficient for selective inhibition if the modifications are positioned correctly (see below). Ghosh et al., furthermore teach that good results are achieved using the end capping/gap technique described under III.

The alternating exchange of every other internucleoside bridge, for example for MeP bridges (Furdan et al., Nucl. Acids Res. 1989, 17, 9193), brings no advantage in comparison with uniformly modified MeP oligonucleotides.

For example, alternatingly MeP-modified oligonucleotides equally do not activate RNase H. A comparison has shown that oligonucleotides with alternating phosphate-O-ethyl or phosphate-O-isopropyl esters and alternating MeP oligonucleotides are also less active than all-MeP or all-PS oligonucleotides [Marcus-Secura et al., Nucl. Acids Res. 1987, 15, 5749].

III) The exchange of one, two or three internucleoside bridges on the 5' or the 3' end of the oligonucleotides (end capping) and the exchange of one, two or three internucleoside bridges on the 5' and the 3' end of the oligonucleotides (gap technique).

As regards the efficacy of end capping, the results are contradictory in some cases. In particular 3' end capping by means of PS, PA or MeP bridges is described as a protection against nucleases [P. D. Cook, supra, Milligan et al., supra]. A protection by means of 3' end capping was also achieved by a series of other modifications. 3'-3' end capping was described by various authors as a protection against nucleolytic degradation [Shaw et al., Nucl. Acids Res. 1991, 19, 747; Seliger et al., Mucleoside & Nucleotides 1991, 10, 469]. A further variant of 3' end capping is the introduction of conjugate molecules on the 3' end, which also increases stability to nucleases, such as, for example, 3'-dodecanol or 3'-acridine [P. D. Cook, supra], or 3-amino-2,3-propanediol [WO92/20697]. The gap technique, ie. the exchange of one, two or three internucleoside bridges on the 5' and the 3' end of the oligonucleotides, has proved particularly advantageous since, apart from PS oligonucleotides, most uniform modifications entail a lose of the capability to activate RNase H and thus a severe loss of activity. Again, a wide range of derivatives, modified phosphodiester bridges, modified sugars, modified bases, such as, for example, MeP-, PS-, PA-, 2'-O-alkyl- or 2'-F-derivatized oligonucleotides, were employed for stabilization purposes. These results are compiled in P. D. Cook supra. Within the gap, a sequence of two to four PO bonds will then suffice to activate RNase H.

Giles et al. [Anti-cancer Drug Design 1993, 8, 33] describe chimeric methylphosphonate-phosphodiester oligonucleotides in which the gap of unmodified PO bridges was reduced continuously from eight to two bridges. While a tendency was found that a reduced gap improved uptake into the cell, the oligonucleotides were not examined for their antisense activity.

An interesting comparison between various strategies can be found in Hoke et al. [Nucl. Acids Res. 1991, 19, 5743]. The authors compare the activity of a range of PS-modified antisense oligonucleotides against HSV-1 in cell culture. Their findings confirm that 3', or 3'+5', end-capped oligonucleotides (the first three internucleoside bridges being modified in each case) in the serum, similarly to all-PS oligonucleotides, are protected sufficiently against degradation by nuclease. In contrast internally modified (3 PS bridges) oligonucleotides and oligonucleotides in which only the 5' end has been capped (again, the first three internucleoside bridges being modified) are degraded rapidly. In contrast, the authors found that neither 5' nor 3' end capping nor both are sufficient for activity within the cell, and they drew the conclusion that a uniform modification (all-PS) is required to achieve sufficient stability to nucleases in cells.

Surprisingly, it has now been found that pyrimidine nucleosides are the weak points in oligonucleotides when it comes to resistance to nucleases. If these sites are now protected by modifications which increase resistance to nucleases, this, in turn, results in a considerably improved stability and activity.

The invention therefore relates to oligonucleotides of the formula

```
ACACCCAATTCTGAAAATGG                  (SEQ ID NO: 1)
                                          (I),

AGGTCCCTGTTCGGGCGCCA                  (SEQ ID NO: 2)
                                          (II),

GTCGACACCCAATTCTGAAAATGGATAA          (SEQ ID NO: 3)
                                          (III),

GCTATGTCGACACCCAATTCTGAAA             (SEQ ID NO: 4)
                                          (IV),

TCGTCGCTGTCTCCGCTTCTTCTTCCTGCCA       (SEQ ID NO: 5)
                                          (V),

CTGTCTCCGCTTCTTCTTCCTGCCATAGGAG       (SEQ ID NO: 6)
                                          (VI),

GCGGGGCTCCATGGGGTCG                   (SEQ ID NO: 7)
                                          (VII),

CAGCTGCAACCCAGC                       (SEQ ID NO: 8)
                                          (VIII),

GGCTGCTGGAGCGGGCACAC                  (SEQ ID NO: 9)
                                          (IX),

AACGTTGAGGGCAT                        (SEQ ID NO: 10)
                                          (X),

CACGTTGAGGGCAT                        (SEQ ID NO: 11)
                                          (XI),

GTGCCGGGGTCTTCGGGC                    (SEQ ID NO: 12)
                                          (XII),

GGAGAACATCATGGTCGAAAG                 (SEQ ID NO: 14)
                                          (XIII),

CCCGAGAACATCATGGTCGAAG                (SEQ ID NO: 15)
                                          (XIV),

GGGGAAAGCCCGGCAAGGGG                  (SEQ ID NO: 16)
                                          (XV),

CACCCGCCTTGGCCTCCCAC                  (SEQ ID NO: 17)
                                          (XVI),

GGGACTCCGGCGCAGCGC                    (SEQ ID NO: 18)
                                          (XVII),

GGCAAACTTTCTTTTCCTCC                  (SEQ ID NO: 19)
                                          (XVIII),

GGGAAGGAGGAGGATGAGG                   (SEQ ID NO: 20)
                                          (XIX),

GGCAGTCATCCAGCTTCGGAG                 (SEQ ID NO: 21)
                                          (XX),

GTCTTCCATAGTTACTCA                    (SEQ ID NO: 22)
                                          (XXI),

GATCAGGCGTGCCTCAAA                    (SEQ ID NO: 23)
                                          (XXII),

TGAAGACGACATGATGTG                    (SEQ ID NO: 24)
                                          (XXIII),

GGCTGCCATGGTCCC                       (SEQ ID NO: 25)
                                          (XXIV),

CTGTAGTTTGACGTGTGGG                   (SEQ ID NO: 26)
                                          (XXV),

GGCCCCTCCAGCCCCACATCCC                (SEQ ID NO: 27)
                                          (XXVI),

GCAGTAAGCATCCATATC                    (SEQ ID NO: 28)
                                          (XXVII),

CCCCCACCACTTCCCCTCTC                  (SEQ ID NO: 29)
                                          (XXVIII),

CTCCCCCACCACTTCCCCTC                  (SEQ ID NO: 30)
                                          (XXIX),

GCTGGGAGCCATAGCGAGG                   (SEQ ID NO: 31)
                                          (XXX),

ACTGCTGCCTCTTGTCTCAGG                 (SEQ ID NO: 32)
                                          (XXXI),

CAATCAATGACTTCAAGAGTTC                (SEQ ID NO: 33)
                                          (XXXII),
``` in which at least one non-terminal pyrimidine nucleoside is modified.

Preferred oligonucleotides are those in which 2–10, in particular 3–6, non-terminal pyrimidine nucleosides are modified, and in which, especially, not more than 8 subsequent nucleotides should be modified. Particular preferred oligonucleotides are those in which additionally the 5' and/or 3' ends are modified, in particular those in which the first 1–5, in particular 1–3, especially 2–3, nucleotides are linked on the 5' and/or 3' end, preferably by phosphorothioate bridges, phosphorodithioate bridges and/or methylphosphonate bridges. Especially preferred are those modified oligonucleotides which contain one or more groups of at least 1–4, in particular 3–4, unmodified nucleotides which are linked to each other. For example, Table 1 shows the antisense oligonucleotide 01 against HSV-1, which is doubly capped with PS on the 5' and 3' end and which is active at a concentration of 27 μM. The introduction of three PS bridges on the 5' and 3' end increases the activity to 9 μM, the same effect being achieved by introducing a further individual PS bridge 3' to a cytosine radical C (antisense oligonucleotide No. 03). The introduction of two PS bridges 5' or 3' to T and C (antisense oligonucleotide No. 05) or the introduction of four PS bridges 5' or 3' to T and C (antisense oligonucleotide No. 06) results in further increases in activity of MIC values (minimum inhibitory concentration) of 3 and 1 μM, respectively. The MIC value of the corresponding all-PS derivative is also 1 μm. This means that it was possible to achieve an increased stability and activity by protecting the pyrimidine nucleosides which was comparable to the all-modified oligonucleotide, but without having to suffer the above-described disadvantages of such a drastic change.

The stabilization on the pyrimidine positions as well as on the 5' and/or 3' ends, independently of one another, can also be effected as follows:

a) Replacement of the 3' and/or the 5' phosphodiester bridge, for example by a phosphorothioate, phosphorodithioate, $NR^1R^2$-phosphoramidate, boranophosphate, phosphate-$(C_1-C_{21})$-O-alkyl ester, phosphate-$[(C_6-C_{12})aryl-(C_1-C_{21})$-O-alkyl] ester, 2,2,2-trichlorodimethylethyl phosphonate, $(C_1-C_8)$-alkyl phosphonate or $(C_6-C_{12})$-aryl phosphonate bridge. The replacement by a phosphorothioate, phosphorodithioate, $NR^1R^2$-phosphoramidate, phosphate-O-methyl ester, phosphate-O-ethyl ester, phosphate-O-isopropyl ester, methyl phosphonate or phenyl phosphonate bridge is preferred. The replacement by a phosphorothioate, phosphorodithioate or methylphosphonate bridge is particularly preferred. The replacement by a phosphorothioate bridge is very particularly preferred.

$R^1$ and $R^2$ independently of one another are hydrogen or $C_1-C_{18}$-alkyl, $C_6-C_{20}$-aryl, $(C_6-C_{14})$-aryl-$(C_1-C_8)$-alkyl, $-(CH_2)_c-[NH(CH_2)_c]_d-NR^3R^3$ in which c is an integer from 2 to 6 and d is an integer from 0 to 6, and $R^3$ radicals independently of one another are hydrogen, $C_1-C_6$-alkyl or $C_1-C_4$-alkoxy-$C_1-C_6$-alkyl; $R^1$ and $R^2$ are preferably hydrogen, $C_1-C_8$-alkyl or methoxyethyl, particularly preferably hydrogen, $C_1-C_4$-alkyl or methoxyethyl. $R^1$ and $R^2$ together with the nitrogen atom to which they are attached can also form a 5-6-membered heterocyclic ring which can additionally contain a further heteroatom from the series consisting of O, S and N.

b) Replacement of the 3' or the 5' phosphodiester bridge by dephospho bridges [see, for example, Uhlmann and Peyman in "Methods in Molecular Biology", Vol. 20: "Protocols for Oligonucleotides and Analogs", S. Agrawal, Ed., Humana Press, Totowa 1993, Chapter 16, 355 et sec.], for example by formacetal, 3'-thioformacetal, methylhydroxylamine, oxime, methylenedimethylhydrazo, dimethylene sulfone or silyl groups. The replacement by formacetals and 3'-thioformacetals is preferred.

c) Replacement of the sugar-phosphate backbone, for example by morpholinonucleoside oligomers [E. P. Stirchak et al., Nucleic Acids Res. 17 (1989) 6129].

d) Replacement of the β-D-2'-deoxyribose, for example by α-D-2'-deoxyribose, L-2'-deoxyribose, 2'-F-2'-deoxyribose, 2'-O-$(C_1-C_6)$alkyl-ribose, 2'-O-$(C_2-C_6)$ alkenyl-ribose, 2'-$NH_2$-2'-deoxyribose, β-D-xylofuranose, α-arabinofuranose, 2,4-dideoxy-β-D-erythro-hexo-pyranose, and carbocyclic [for example Froehler, J. Am. Chem. Soc. 1992, 114, 8320] and open-chain sugar analogs [for example Vandendriessche et al., Tetrahedron 1993, 49, 7223] or bicyclo sugar analogs [for example M. Tarkov et al., Helv. Chim. Acta 1993, 76, 481]. The replacement by 2'-F-2'deoxyribose, 2'-O-$(C_1-C_6)$alkyl-ribose, 2'-O-$(C_2-C_6)$ alkenyl-ribose or 2'-$NH_2$-2'-deoxyribose is preferred. The replacement by 2'-F-2'-deoxyribose, 2'-O-$(C_1-C_4)$ alkyl-ribose or 2'-O-$(C_2-C_4)$alkenyl-ribose or 2'-$NH_2$-2'-deoxyribose is particularly preferred. The replacement by 2'-O-methyl-, 2'-O-allyl- or 2'-O-butyl ribose is very particularly preferred.

e) Replacement of the natural nucleoside bases, for example by 5-(hydroxymethyl)uracil, 5-aminouracil, pseudouracil, dihydrouracil, 5-$(C_1-C_6)$-alkyluracil, 5-$(C_2-C_6)$-alkenyluracil, 5-$(C_2-C_6)$-alkynyluracil, 5-$(C_1-C_6)$-alkylcytosine, 5-$(C_2-C_6)$-alkenylcytosine, 5-$(C_2-C_6)$-alkynylcytosine, 5-fluorouracil, 5-fluorocytosine, 5-chlorouracil, 5-chlorocytosine, 5-bromouracil or 5-bromocytosine. The replacement by 5-$(C_1-C_6)$-alkyluracil, 5-$(C_2-C_6)$-alkenyluracil, 5-$(C_2-C_6)$-alkynyluracil, 5-$(C_1-C_6)$-alkylcytosine, 5-$(C_2-C_6)$-alkenylcytosine, 5-$(C_2-C_6)$-alkynylcytosine, 5-fluorouracil, 5-fluorocytosine, 5-chlorouracil, 5-chlorocytosine, 5-bromouracil or 5-bromocytosine is preferred. The replacement by 5-$(C_3-C_6)$-alkyluracil, 5-$(C_2-C_6)$-alkenyluracil, 5-$(C_2-C_6)$-alkynyluracil, 5-$(C_1-C_6)$-alkylcytosine, 5-$(C_2-C_6)$-alkenylcytosine or 5-$(C_2-C_6)$-alkylcytosine is particularly preferred. The replacement by 5-pentynylcytosine, 5-hexynylurasil or 5-hexynylcytosine is very particularly preferred.

Amongst the abovementioned modifications, specially preferred modifications are those of groups a), b), c) and d), especially groups a) and d), in particular group a).

In addition, the oligonucleotides according to the invention can be linked (conjugated), for example on the 3' and/or 5' end, with molecules which have an enhancing effect on the characteristics of antisense oligonucleotides or of triple-helix-forming oligonucleotides (such as, for example, cell penetration, degradation by nuclease, affinity to the target RNA/DNA, pharmaco-kinetics). Examples are conjugates with poly-lysine, with intercalaters such as pyrene, acridine, phenazine, phenanthridine, with fluorescent compounds such as fluorescein, with crosslinkers such as psoralens, azido-proflavin, and with lipophilic molecules such as $C_{12}-C_{20}$-alkyl, or with derivatives thereof, such as, for example, hexamethylenetetraamine, with terpenes such as farnesol or phytol, with lipids such as 1,2-dihexadecyl-rac-glycerol, with steroids such as gallic acid, cholesterol or testosterone, with vitamins such as vitamin E, with poly- or oligoethylene glycol, with $(C_{12}-C_{18})$-alkyl phosphate-diesters or with —O—$CH_2$—CH(OH)—O—$(C_{12}-C_{18})$-alkyl. Conjugates with lipophilic molecules such as $C_{12}-C_{20}$-alkyl, with steroids such as cholesterol or testosterone, with poly- or oligoethylene glycol, with vitamin E, with intercalaters such as pyrene, with $(C_{14}-C_{18})$-alkyl phosphate diesters or with —O—$CH_2$—CH(OH)—O—$(C_{12}-C_{16})$-alkyl are preferred.

The preparation of such oligonucleotide conjugates is known to a person skilled in the art (see, for example, Uhlmann & Peyman, Chem. Rev. 1990, 90, 543; M. Manoharan in Antisense Research and Applications, Crooke and Lebleu, Eds. CRC Press, Boca Raton, 1993, Chapter 17, pp. 303 et seq., EP0552766A2).

Moreover, the oligonucleotides according to the invention can carry 3'-3' and 5'-5' inversions [described, for example, in M. Koga et al., J. Org. Chem. 56 (1991) 3757] on the 3' and/or the 5' end.

The invention furthermore relates to processes for the preparation of the compounds according to the invention by processes known to a person skilled in the art, in particular chemical synthesis, to the use of the compounds according to the invention for the preparation of a pharmaceutical, and to a process for the preparation of a pharmaceutical which comprises mixing the oligonucleotides according to the invention with a physiologically acceptable excipient and, if appropriate, suitable additives and/or auxiliaries.

Quite generally, the present invention also extends to the use of therapeutically active oligonucleotides for the preparation of a pharmaceutical in which at least one non-terminal pyridine nucleoside is modified. Therapeutically active oligonucleotides are generally to be understood as meaning antisense oligonucleotides, triple-helix-forming oligonucleotides, aptamers (RNA or DNA molecules which can bind to specific target molecules, for example proteins or receptors (for example L. C. Bock et al., Nature 1992, 355, 564) or ribozymes (catalytic RNA, see, for example, Castanetto et al., Critical Rev. Eukar. Gene Expr. 1992, 2, 331), in particular antisense oligonucleotides.

Moreover, the present invention furthermore relates to the use of oligonucleotides having at least one non-terminal and modified pyrimidine nucleoside as a diagnostic, for example for detecting the presence or absence or the amount of a specific double-stranded or single-stranded nucleic acid molecule in a biological sample.

For their use according to the invention, the oligonucleotides have a length of approximately 6–100, preferably approximately 10–40, in particular approximately 12–25, nucleotides. Again, the above-described preferred ranges, modifications and conjugations apply.

The pharmaceuticals of the present invention can be used for example for the treatment of diseases caused by viruses, for example by HIV, HSV-1, HSV-2, influenza, VSV, hepatitis B or papilloma viruses.

Examples of antisense oligonucleotides according to the invention which are active against such targets are:

a) against HIV, for example

```
5'-A*C*A*C C*C A A T*T*C*T G A A A A*T*G*G-3' or                    (SEQ ID NO: 1)

5'-A*C*A C*C*C A A*T T*C T*G A A A A*T*G*G-3' or

5'-A*C*A C*C C A A T*T*C*T G A A A A T*G*G-3'
                          (I)

5'-A*G*G T*C C*C*T G T*T*C G G G C G C*C*A-3' or                   (SEQ ID NO: 2)

5'-A*G*G T*C C*C*T G*T T*C G G G C G C*C*A-3' or

5'-A*G*G T*C C*C*T G T*T*C G G G C G C*C*A-3'
                          (II)

5'-G*T*C G A*C A C*C C A A T*T C*T G A A A A T*G G A T*A*A-3' or   (SEQ ID NO: 3)

5'-G*T*C G A*C A C*C*C A A T*T C*T G A A A A T*G G A T*A*A-3' or

5'-G*T*C G A*C A C*C*C A A T*T C*T G A A A A T*G G A*T*A*A-3' or

5'-G*T*C*G A*C A C*C*C A A T*T*C*T G A A A A T*G G A*T*A*A-3'
                          (III)

5'-G*C*T A T G T*C G A*C A C C*C A A T*T*C*T*G A*A*A-3' or         (SEQ ID NO: 4)

5'-G*C*T A T*G T*C G A*C A C C*C A A T*T*C*T*G A*A*A-3' or

5'-G*C*T A T*G T*C G A C A C*C C*A A T*T C*T G A*A*A-3' or

5'-G*C*T A T*G T*C G A C*A C*C C*A A T*T C*T G A*A*A-3' or

5'-G*C*T A T G T*C G A C A C*C C*A A T*T C*T G A*A*A-3'
                          (IV)

5'-T*C*G*T*C G C*T G T C*T*C*C G C T*T C T T C T T C C T*G*C*C*A or (SEQ ID NO: 5)

5'-T*C*G*T*C G C*T G T C*T*C*C G C T*T C T*T C T T C C T*G*C*C*A or

5'-T*C*G*T*C G C*T G T*C*T*C*C G C T*T*C T*T*C T T*C C T*G*C*C*A or

5'-T*C*G*T*C G C*T G T C*T*C*C G C T*T C T*T*C*T*T C C T*G*C*C*A or

5'-T*C*G*T*C G C*T G T*C*T*C*C G C T*T*C T*T*C T T C C T*G*C*C*A or

5'-T*C*G T*C G C*T G T*C*T*C*C G C T*T*C T*T*C T*T C*C*T G C*C*A
                          (V)

5'-C*T*G T C T*C*C G C T*T C*T T*C T*T C*C T G C*C A T A G G*A*G or (SEQ ID NO: 6)

5'-C*T*G T C T*C*C G C*T*T C T*T*C*T T*C C*T G C*C A T A G G*A*G or
```

-continued
```
5'-C*T*G T*C*T C C G C*T T*C*T T C*T*T*C*C T G C*C A T A G G*A*G or 5'-C*T*G T C*T C C G C*T T*C*T*T C*T*T C*C T G C*C A T A G G*A*G or
                                    (VI)
``` b) against HSV-1, for example

```
5'-G*C*G G G G C T C C*A T G G G G G T*C*G-3' or     (SEQ ID NO: 7)

5'-G*C*G G G G C*T C C A*T G G G G G T*C*G-3' or

5'-G*C*G G G G C*T C*C*A*T G G G G G T*C*G-3'
                        (VII)
```

The pharmaceuticals of the present invention are also suitable, for example, for the treatment of cancer. For example, oligonucleotide sequences can be used which are directed against targets responsible for the formation or growth of cancer. Examples of such targets are:

1) Nuclear oncoproteins such as, for example, c-myc, N-myc, c-myb, c-fos c-fos/jun, PCNA, p.120

2) Cytoplasmic/membrane-associated oncoproteins such as, for example, EJ-ras, c-Ha-ras, N-ras, rrg, bcl-2, cdc-2, c-raf-1, c-mos, c-src, c-abl 3) Cellular receptors such as, for example, EGF receptor, c-erbA, retinoid receptors, protein-kinase-regulatory subunit, c-fms 4) Cytokins, growth factors, extracellular matrix such as, for example, CSF-1, IL-6, IL-1a, IL-1b, IL-2, IL-4, bFGF, myeloblastin, fibronectin.

Antisense oligonucleotides according to the invention which are active against such targets are, for example, a) against c-Ha-ras, for example,

```
                                                      (SEQ ID NO: 8)
5'-C*A*G C*T G*C A A C*C*C A*G*C-3' or

5'-C*A*G*C T G C A A C*C C*A*G*C-3' or

5'-C*A*G*C T G C*A A C*C C*A*G*C-3' or

5'-C*A*G*C T G*C*A A C*C C*A*G*C-3' or

5'-C*A*G*C*T G*C A A C*C C*A*G*C-3' or

5'-C*A*G*C T*G C*A A C*C*C*A*G*C-3'
                (VIII)
``` c) c-myc, for example,

```
                                                      (SEQ ID NO: 9)
5'-G*G*C*T G C*T G G A G*C G G G G*C A C*A*C-3' or

5'-G*G*C T G C*T G G A G C G G G G C*A C*A*C-3' or

5'-G*G*C*T G C*T G G A G*C G G G G C*A*C*A*C-3' or

5'-G*G*C*T G C*T*G G A G*C*G G G G*C A C*A*C-3' or
                                           (IX)

(SEQ ID NO: 10)
5'-A*A*C G T*T G A G G G G C*A*T-3' or

5'-A*A*C*G T*T G A G G G G*C*A*T-3' or

5'-A*A*C*G*T T*G A G G G G*C*A*T-3' or
                                           (X)

(SEQ ID NO: 11)
5'-C*A*C*G T*T*G A G G G G*C*A*T-3'  (XI)
``` d) c-myb, for example,

```
                                                      (SEQ ID NO: 12)
5'-G*T*G C*C G G G G T*C*T*T C G G*G*C 3' or

5'-G*T*G C*C G G G G T*C T*T*C G G*G*C 3' or

5'-G*T*G C*C*G G G T*C T*T*C G G*G*C-3' or

5'-G*T*G*C C*G G G G T*C T*T*C G G*G*C-3' or

5'-G*T*G C*C G G G G*T C*T T*C G G*G*C-3'
                      (XII A)

(SEQ ID NO: 13)
5'-G*T*G*T C*G G G G T*C*T C*C G*G*G*C-3' (mouse)
                      (XII B)
``` e) c-fos, for example,

```
5'-G*G*A G A A C*A T*C A T*G G T*C G A A*A*G-3' or     (SEQ ID NO: 14)

5'-G*G*A G A A*C A T*C A T*G G T*C G A A*A*G-3' or

5'-G*G*A*G A A C*A T*C A T*G G T*C G A*A*A*G-3' or

5'-G*G*A G A A C*A*T*C A T*G G T*C G A A*A*G-3' or

5'-G*G*A G A A*C*A T*C*A*T G G T*C G A A*A*G-3' or
                            (XIII)

5'-C*C*C*G A G A A*C A T*C A T*G G T*C G A*A*G-3' or   (SEQ ID NO: 15)

5'-C*C*C G A G A A C*A T*C A*T G G T*C G A*A*G-3'
```

-continued (XIV)

5'-G*G*G G A A A G C*C*C G G*C A A G G*G*G-3' or  (SEQ ID NO: 16)

5'-G*G*G G A A A G C*C C*G G C*A A G G*G*G-3'
(XV)

f) p120, for example, (SEQ ID NO: 17)
5'-C*A*C*C C*G C*C T*T G G C C T*C C*C*A*C-3' or 5'-C*A*C*C*G C C*T*T G G C C*T C C*C*A*C-3' or 5'-C*A*C C*C*G C*C T*T G G C C T*C*C C*A*C-3' or 5'-C*A*C*C C G C C T*T G G C C T*C C*C*A*C-3' or 5'-C*A*C*C C G C*C T*T G G C C*T C C*C*A*C-3' or
(XVI)

g) EGF receptor, for example, (SEQ ID NO: 18)
5'-G*G*G A C*T*C*C G G*C G*C A G C*G*C-3' or 5'-G*G*G A*C T*C*C G G*C G*C A G C*G*C-3' or

5'-G*G*G A C T*C*C G G*C G*C A G C*G*C-3'
(XVII)

(SEQ ID NO: 10)
5'-G*G*C A A A C T*T*T C T T*T*T C C T*C*C-3' or

5'-G*G*C A A A C*T T*T*C T T*T T C C*T*C*C-3' or

5'-G*G*C A A A C*T*T T C*T T*T T C C*T*C*C-3' or

5'-G*G*C A A A C*T*T T C T*T T*T C*C T*C*C-3'
(XVIII)

h) p 53 tumor suppressor, for example, (SEQ ID NO: 20)
5'-G*G*G A A G G A G G A G G A T*G A*G*G-3' or

5'-G*G*G*A A G G A G G A G G A*T G*A*G*G-3'
(XIX)

(SEQ ID NO: 21)
5'-G*G*C A G T*C A T*C*C A G C*T T*C G G*A*G-3' or

5'-G*G*C A G T*C A T*C C A G C*T T*C G G*A*G-3' or

5'-G*G*C A G*T C*A*T C*C A G*C T*T C G G*A*G-3'
(XX)

j) Antisense oligonucleotide against cdc2 kinase:

5'-G*T*C*TTC*CAT*AGT*TAC*
T*C*A-3' (XXI)  (SEQ ID NO: 22)

k) Antisense oligonucleotide against PCNA (proliferating cell nuclear antigen):

5'-G*A*T*CAGG*CG*TGC*CTC*
A*A*A-3' (XXII)  (SEQ ID NO: 23)

l) Antisense oligonucleotide against IGF-1:

5'-T*G*A*AGA*CGAC*A*TGAT*G*
T*G-3' (XXIII)  (SEQ ID NO: 24)

m) Antisense oligonucleotide against bFGF translation start site:

5'-G*G*C*TGC*CA*TGGT*C*C*C-3'

5'-farnesyl-G*G*C*TGC*CA*TGGT*C*C*C-3'

5'-phytyl-G*G*C*TGC*CA*TGGT*C*C*C-3'

5'-hexadecyl-G*G*C*TGC*CA*TGGT*C*C*C-3'

5'-cholesteryl-G*G*C*TGC*CA*TGGT*C*C*C-3'

5'-hexamethylenetetraamine-G*G*C*TGC*CA*TGGT*C*C*C-3'

5'-G*G*C*TGC*CA*TGGT*C*C*C-hexadecyl-3'

5'-G*G*C*TGC*CA*TGGT*C*C*C-cholesteryl-3'

5'-G*G*C*TGC*CA*TGGT*C*C*C-vitamin E-3'

5'-G*G*C*TGC*CA*TGGT*C*C*C-
bile acid-3' (XXIV)  (SEQ ID NO: 25)

n) Antisense oligonucleotide against bFGF codon 58 ff

5'-C*T*G*TAGT*T*TGAC*G*TGT*G*
G*G-3' (XXV)  (SEQ ID NO: 26)

o) Antisense oligonucleotide against FGF receptor:

5'-G*G*C*CCC*T*CCAGC*CC*CACAT*
C*C*C-3' (XXVI)  (SEQ ID NO: 27)

Furthermore, the pharmaceuticals of the present invention are suitable, for example, for treatment of diseases affected by integrins or cell-cell adhesion receptors, for example by VLA-4, VLA-2, ICAM or ELAM.

Antisense oligonucleotides according to the invention which are active against such targets are, for example, a) VLA-4, for example, (SEQ ID NO: 28)
5'-G*C*A G*T A A G C*A T*C*C A T*A*T*C -3' or

5'-G*C*A G*T A A G*C A T*C*C A T*A*T*C -3'
(XXVII)

b) ICAM, for example, (SEQ ID NO: 29)
5'-C*C*C C C A C*C A C T*T*C*C C C T C*T*C-3' or 5'-C*C*C*C C A C*C A C T*T*C*C C C T*C*T-3' or

5'-C*C*C*C C A*C C*A C T*T*C*C C C*T*C*T*C-3'
(XXVIII)

(SEQ ID NO: 30)
5'-C*T*C*C C C C A C*C A C T*T C C C*C*T*C-3' or

-continued

5'-C*T*C*C*C C C A C*C A C T*T C C*C*C*T*C-3' or
(XXIX)

(SEQ ID NO: 31)
5'-G*C*T G G G A G C*C A*T A G*C G A*G*G-3' or

5'-G*C*T G G G A G C*C A T*A G*C*G A*G*G-3'
(XXX)

c) ELAM-1, for example,

5'-A*C*T G C*T G C*C T*C T*T G T*C T*C A*G*G-3' or  (SEQ ID NO: 32)
5'-A*C*T G C T G C*C T*C T*T G T*C T C A*G*G-3'
(XXXI)
5'-C*A*A T*C A A T*G A C*T T*C A A G A G T*T*C-3' or  (SEQ ID NO: 33)
5'-C*A*A T C A A T*G A C*T T*C A A G A G T*T*C-3'
(XXXII)

The pharmaceuticals can be used for example in the form of drug preparations which can be administered orally, for example in the form of tablets, coated tablets, hard- or soft-gelatin capsules, solutions, emulsions or suspensions. They can also be administered rectally, for example in the form of suppositories, or parenterally, for example in the form of injectable solutions. For the preparation of drug preparations, these compounds can be incorporated into therapeutically inert organic and inorganic excipients. Examples of such excipients for tablets, coated tablets and hard-gelatin capsules are lactose, corn starch or derivatives thereof, tallow and stearic acid or salts thereof. Suitable excipients for the preparation of solutions are water, polyols, sucrose, invert sugars and glucose. Suitable excipients for injectable solutions are water, alcohols, polyols, glycerol and vegetable oils. Suitable excipients for suppositories are vegetable and hardened oils, waxes, fats and semi-liquid polyols. The drug preparations can also comprise preservatives, solvents, stabilizers, wetting agents, emulsifiers, sweeteners, colorants, flavorings, salts for regulating the osmotic pressure, buffers, coating agents, antioxidants and, if appropriate, other therapeutic active substances. A preferred form of administration is an injection. To this end, the antisense oligonucleotides are formulated in a liquid solution, preferably in a physiologically acceptable buffer such as, for example, Hank's solution or Ringer's solution. However, the antisense oligonucleotides can also be formulated in solid form and dissolved or suspended prior to use. The doses preferred for systematic administration are approximately 0.01 mg to approximately 50 mg per kg of body weight per day.

The examples which follow are intended to illustrate the invention in greater detail.

EXAMPLE 1

Oligonucleotide Synthesis

Unmodified oligonucleotides were synthesized using an automatic DNA synthesizer (Applied Biosystems Model 380B or 394) using the standard phosphoramidite chemistry and oxidation with iodine. To introduce phosphorothioate bridges in mixed phosphorothioates and phosphodiester oligonucleotides, the oxidation was carried out using TETD (tetraethylthiuram disulfide) instead of iodine (Applied Biosystems User Bulletin 65). After the oligonucleotides had been removed from the solid support (CPG or Tentagel) and the protective groups had been eliminated at 55° C. for 18 h using concentrated $NH_3$, the oligonucleotides were first purified by precipitation with butanol (Sawadogo, Van Dyke, Nucl. Acids Res. 19 (1991) 674). The sodium salt was then obtained by precipitation from an 0.5 M NaCl solution using 2.5 parts by volume of ethanol.

The [4-(1-pyrenyl)butanyl] phosphodiester was introduced on the 5' end as described in J. S. Mann et al. Bioconj. Chem. 3 (1992) 554.

The oligonucleotides were analyzed as follows:
a) Analytic gel electrophoresis in 20% acrylamide, 8 M urea, and/or
b) HPLC analysis: Waters GenPak FAX, gradient from $CH_3CN$ (400 ml), $H_2O$ (1.6 l), $NaH_2PO_4$ (3.1 g), NaCl (11.7 g), pH 6.8 (0.1 M NaCl) to $CH_3CN$ (400 ml), $H_2O$ (1.6 l), $NaH_2PO_4$ (3.1 g), NaCl (175.3 g), pH 6.8 (1.5 M NaCl) and/or
c) Capillary gel electrophoresis Beckmann capillary eCAP™, U100P gel column, 65 cm length, 100 mm I.D., window 15 cm from one end, buffer 140 μM Tris, 360 mM boric acid, 7 M urea, and/or
d) Electrospray mass spectroscopy.

Analysis of the oligonucleotides revealed that their purity was in each case greater than 90%.

The structures of the oligonucleotides synthesized are shown in Table 1.

EXAMPLE 2

Test for antiviral activity of test substances against herpes viruses in vitro.

The antiviral activity of the test substances against a range of herpes viruses with are pathogenic to humans is tested in a cell-culture test system.

For the test, monkey kidney cells (Vero, $2 \times 10^5$/ml) are seeded into serum-containing Dulbecco's MEM (5% fetal calf serum FCS) in 96-well microtiter plates and incubated for 24 hours at 37° C. with 5% $CO_2$. The serum-containing medium is then removed by suction, and cells are washed twice using serum-free Dulbecco's MEM (-FCS).

The test substances are prediluted with $H_2O$ to a concentration of 600 μM and stored at -18° C. To carry out the test, more predilution steps are performed in Dulbecco's minimal essential medium (MEN). 100 μl of the individual test substance dilutions together with 100 μl of serum-free Dulbecco's MEM (-FCS) are added to the washed cells.

After incubation for 3 hours at 37° C. with 5% $CO_2$, the cells are infected with Herpes simplex virus type 1 (ATCC VR733, HSV-1 F strain) or with Herpes simplex virus type 2 (ATCC VR734, HSV-2 G strain) using concentrations which completely destroy the cell sheet within 3 days. In the case of HSV-1, the infection density is 500 plaque-forming units (PFU) per well, in the case of HSV-2 350 PRU/well. The test batches then contain test substance at concentrations of 80 μM to 0.04 μM in MEM supplemented with 100 U/ml of penicillin G and 100 mg/l of streptomycin. Two replications are carried out for each test, with the exception of the controls, for which are replicated eight times per plate.

The batches are incubated for 17 h at 37° C. with 5% $CO_2$. The cytotoxicity of the test substances is determined after total incubation time of 20 h by viewing the cell cultures under the microscope. The term dosis tolerata maxima (DTM) is used to designate the highest concentration of the preparation which does not cause any cell damage under the abovementioned test conditions which can be observed under the microscope.

Then, FCS is added to an end concentration of 4%, followed by further incubation for 55 h at 37° C. with 5% $CO_2$. A complete cytopathic effect (CPE) can then be observed in the untreated infection controls. After the cell cultures have been viewed under the microscope, they are stained with Neutral Red following the vital stain method described by Finter (1966). The antiviral activity of a test substance is defined as the minimum inhibitory concentration (MIC) required for protecting 30–60% of the cells against the cytopathogenic effect caused by the virus.

Table 1: Activity of variously modified antisense oligonucleotides against HSV-1 in cell culture. The phosphodiester bonds replaced by a phosphorothioate bridge (P=S) were labelled with an * in the sequence:

TABLE 1

Activity of variously modified antisense oligonucleotides against HSV-1 in cell culture. The phosphodiester bonds replaced by a phosphorothioate bridge (P = S) were labelled with an * in the sequence:

| No. | Sequence | MTC | (DTM) |
|---|---|---|---|
| 01 (S92 6418) | G*C*GGGGCTCCATGGGGGT*C*G | 27 | (>80) |
| 03 (S93 1558) | G*C*GGGGCTCC*ATGGGGGT*C*G | 9 | (>80) |
| 04 (S93 1559) | G*CGGGGCTCCATGGGGGTC*G | 80 | (>80) |
| 05 (S93 1560) | G*C*GGGGC*TCCA*TGGGGGT*C*G | 3 | (>80) |
| 06 (S93 1561) | G*C*GGGGC*TC*C*A*TGGGGGT*C*G | 1 | (>80) |
| 07 (S93 1725) | GCGGGGCTCCATGGGG*T*C*G | 27 | (>80) |
| 08 (S93 1725) | G*C*G*GGGCTCCATGGGGGTCG | 27 | (>80) |
| 09 (S93 2736) | G*C*G*G*G*G*C*T*C*C*A*T*G*G*G*G*T*C*G | 1 | (>80) |

In the above Table 1, each oligonucleotide listed is a modified version of SEQ. ID NO. 7.

EXAMPLE 3

Test for antiproliferative activity of test substances in smooth cell muscles.

The oligonucleotides listed below were tested for their ability of inhibiting the proliferation of smooth cell muscles. The test was carried out as described in S. Biro et al., [Proc. Natl. Acad. Sci. USA 90 (1993) 654]. All oligonucleotides were active in a range of 5 to 20 μM. The phosphodiester bonds replaced by a phosphorothioate bridge (P=S) were labelled with a * in the sequence.

1) Antisense oligonucleotide against cdc2 kinase:

5'-G*T*C*TTC*CAT*AGT*TAC*T*C*A-3'  (SEQ ID NO: 22)

2) Antisense oligonucleotide against PCNA (proliferating cell nuclear antigen):

5'-G*A*T*CAGG*CG*TGC*CTC*A*A*A-3'  (SEQ ID NO: 23)

3) Antisense oligonucleotide against IGF-1:

5'-T*G*A*AGA*CGAC*A*TGAT*G*T*G-3'  (SEQ ID NO: 24)

4) Antisense oligonucleotide against mouse c myb:

5'-G*T*G*TC*GGGGT*C*TC*CG*G*G*C-3'  (SEQ ID NO:13)

5) Antisense oligonucleotide against bFGF translation start site:

5'-G*G*C*TGC*CA*TGGT*C*C*C-3'

5'-farnesyl-G*G*C*TGC*CA*TGGT*C*C*C-3'

5'-phytyl-G*G*C*TGC*CA*TGGT*C*C*C-3'

5'-hexadecyl-G*G*C*TGC*CA*TGGT*C*C*C-3'

5'-cholesteryl-G*G*C*TGC*CA*TGGT*C*C*C-3'

5'-hexamethylenetetraamine-G*G*C*TGC*CA*TGGT*C*C*C-3'

5'-G*G*C*TGC*CA*TGGT*C*C*C-hexadecyl-3'

5'-G*G*C*TGC*CA*TGGT*C*C*C-cholesteryl-3'

5'-G*G*C*TGC*CA*TGGT*C*C*C-vitamin E-3'

5'-G*G*C*TGC*CA*TGGT*C*
  C*C-bile acid -3'  (SEQ ID NO: 25)

6) Antisense oligonucleotide against bFGF codon 58ff:

5'-C*T*G*TAGT*T*TGAC*G*TGT*G*G*G-3' (SEQ ID NO: 26)

7) Antisense oligonucleotide against FGF receptor:

5'-G*G*C*CCC*T*CCAGC*CC*CACAT*
  C*C*C-3'  (SEQ ID NO: 27)

8) Antisense oligonucleotide against c-myc:

5'-C*A*C*GT*T*GAGGGG*C*A*T-3'  (SEQ ID NO: 11)

What is claimed is:

1. An oligonucleotide having a length of 6–100 nucleotides, wherein at least one non-terminal pyrimidine nucleoside is modified, and wherein additionally the 5' and/or 3' ends are modified, with the proviso that less than all nucleotides of said oligonucleotide are modified and that phosphorothioate modifications follow a pattern other than $(PS-PO-PO-PO)_n$ or $((PO)_2-(PS)_2)_n$, wherein n=4, $(PS-PO)_n$ or $(PO-PS)_n$, wherein n=8, and wherein each modification is the replacement of a 3' and/or 5' phosphodiester bridge by a phosphorothioate bridge.

2. An oligonucleotide as claimed in claim 1, wherein 2–10 non-terminal pyrimidine nucleosides are modified.

3. An oligonucleotide as claimed in claim 1, wherein 3–6 non-terminal pyrimidine nucleosides are modified.

4. An oligonucleotide as claimed in claim 1, wherein the oligonucleotide has a length of 10 to 40 nucleotides.

5. An oligonucleotide as claimed in claim 4, wherein 4 nonterminal pyrimidine nucleosides are modified.

6. An oligonucleotide as claimed in claim 4, wherein 2–10 non-terminal pyrimidine nucleosides are modified.

7. An oligonucleotide as claimed in claim 4, wherein 3–6 non-terminal pyrimidine nucleosides are modified.

8. An oligonucleotide as claimed in claim 4, having a sequence selected from the group consisting of: SEQ ID NO. 1 (I), SEQ ID NO. 2 (II), SEQ ID NO. 3 (III), SEQ ID NO. 4 (IV), SEQ ID NO. 5 (V), SEQ ID NO. 6 (VI), SEQ ID NO. 7 (VII), SEQ ID NO. 8 (VIII), SEQ ID NO. 9 (IX), SEQ ID NO. 10 (X), SEQ ID NO. 11 (XI), SEQ ID NO. 12 (XIIA), SEQ ID NO. 13 (XIIB), SEQ ID NO. 14 (XIII), SEQ ID NO. 15 (XIV), SEQ ID NO. 16 (XV), SEQ ID NO. 17 (XVI), SEQ ID NO. 18 (XVII), SEQ ID NO. 19 (XVIII), SEQ ID NO. 20 (XIX), SEQ ID NO. 21 (XX), SEQ ID NO. 22 (XXI), SEQ ID NO. 23 (XXII), SEQ ID NO. 24 (XXIII), SEQ ID NO. 25 (XXIV), SEQ ID NO. 26 (XXV), SEQ ID NO. 27 (XXVI), SEQ ID NO. 28 (XXVII), SEQ ID NO. 29 (XXVIII), SEQ ID NO. 30 (XXIX), SEQ ID NO. 31 (XXX), SEQ ID NO. 32 (XXXI), and SEQ ID NO. 33 (XXXII).

9. An oligonucleotide as claimed in claim 1, wherein the oligonucleotide has a length of 12 to 25 nucleotides.

10. An oligonucleotide as claimed in claim 9, wherein 3–6 non-terminal pyrimidine nucleosides are modified.

11. An oligonucleotide as claimed in claim 1, wherein the oligonucleotide has a length of 19 nucleotides.

12. An oligonucleotide as claimed in claim 11, wherein 2–10 non-terminal pyrimidine nucleosides are modified.

13. An oligonucleotide as claimed in claim 11, wherein 3–6 non-terminal pyrimidine nucleosides are modified.

14. An oligonucleotide as claimed in claim 11, wherein 4 nonterminal pyrimidine nucleosides are modified.

15. An oligonucleotide as claimed in claim 11, wherein the first 1 to 5 nucleotides at the 5' end and/or the first 1 to 5 nucleotides at the 3' end are modified.

16. An oligonucleotide as claimed in claim 11, wherein the first 1 to 3 nucleotides at the 5' end and/or the first 1 to 3 nucleotides at the 3' end are modified.

17. An oligonucleotide as claimed in claim 11, wherein the first 2–3 nucleotides at the 5' end and/or the 3' end are modified.

18. An oligonucleotide as claimed in claim 11, wherein the first 2 nucleotides at the 5' end and the first 5 nucleotides at the 3' end are modified.

19. An oligonucleotide as claimed in claim 11, wherein the first 3 nucleotides at the 5' end and the first 5 nucleotides at the 3' end are modified.

20. An oligonucleotide as claimed in claim 11, which contains one or more groups of 1 to 4 unmodified nucleotides which are linked to each other.

21. An oligonucleotide as claimed in claim 11, which contains 2 groups with 1 unmodified nucleotide.

22. An oligonucleotide as claimed in claim 11, which contains one or more groups of 3 to 4 unmodified nucleotides which are linked to each other.

23. An oligonucleotide as claimed in claim 11, wherein the oligonucleotide sequence is directed against targets responsible for the formation or growth of cancer.

24. A method of preparing a pharmaceutical agent wherein an oligonucleotide of claim 11 is combined with a pharmaceutically acceptable excipient.

25. A method of preparing a diagnostic reagent wherein an oligonucleotide of claim 11 is combined with an acceptable carrier.

26. A method of inhibiting the expression of a specific target comprising the steps of:

(a) bringing an oligonucleotide of claim 11 in contact with the target; and (b) hybridizing the oligonucleotide with the target, wherein the oligonucleotide functions as an antisense oligonucleotide, a triple-helix forming oligonucleotide, an adaptamer, or a ribozyme.

27. A method of inhibiting the expression of a specific target comprising the steps of:

(a) bringing an oligonucleotide of claim 11 in contact with the target; and (b) hybridizing the oligonucleotide with the target.

28. A pharmaceutical composition comprising an oligonucleotide as claimed in claim 11, wherein the oligonucleotide may be used in the treatment of cancer.

29. A method of treating cancer comprising administering to a patient in need of treatment, a pharmaceutical composition as claimed in claim 28.

30. A pharmaceutical composition comprising an oligonucleotide as claimed in claim 11, wherein the oligonucleotide may be used in the treatment of a viral disease.

31. A method of treating a viral infection comprising administering to a patient in need of treatment, a pharmaceutical composition as claimed in claim 30.

32. A pharmaceutical composition comprising an oligonucleotide as claimed in claim 11, wherein the oligonucleotide may be used in the treatment of a disease affected by or involving integrins or cell-cell adhesion receptors.

33. A method of treating a disease affected by or involving integrins or cell-cell adhesion receptors comprising administering to a patient in need of treatment, a pharmaceutical composition as claimed in claim 32.

34. An oligonucleotide as claimed in claim 1, wherein the first 1 to 5 nucleotides at the 5' end and/or the first 1 to 5 nucleotides at the 3' end are modified.

35. An oligonucleotide as claimed in claim 1, wherein the first 1 to 3 nucleotides at the 5' end and/or the first 1 to 3 nucleotides at the 3' end are modified.

36. An oligonucleotide as claimed in claim 1, wherein the first 2–3 nucleotides at the 5' end and/or the 3' end are modified.

37. An oligonucleotide as claimed in claim 1, wherein the first 2 nucleotides at the 5' end and the first 5 nucleotides at the 3' end are modified.

38. An oligonucleotide as claimed in claim 1, wherein the first 3 nucleotides at the 5' end and the first 5 nucleotides at the 3' end are modified.

39. An oligonucleotide as claimed in claim 1, which contains one or more groups of 1 to 4 unmodified nucleotides which are linked to each other.

40. An oligonucleotide as claimed in claim 1, which contains 2 groups with 1 unmodified nucleotide.

41. An oligonucleotide as claimed in claim 1, which contains one or more groups of 3 to 4 unmodified nucleotides which are linked to each other.

42. An oligonucleotide as claimed in claim 1, wherein the oligonucleotide is directed against targets responsible for the formation or growth of cancer.

43. An oligonucleotide as claimed in claim 42, wherein the oligonucleotide binds to a target selected from a nuclear oncoprotein, a cytoplasmic- or membrane-associated oncoprotein, a cellular receptor, and a cytokins, a growth factors, and an extracellular matrix.

44. An oligonucleotide as claimed in claim 42, wherein the oligonucleotide binds to a target selected from c-myc, N-myc, c-fos, c-fos/jun, PCNA, p. 120, EJ-ras, c-Ha-ras, N-ras, rrg, bcl-2, cdc-2, c-raf-1, c-mos, c-src, c-abl, EGF receptor, c-erbA, retinoid receptor, protein-kinase- regulatory subunit, c-fms, CSF-1, IL-6, IL-1a, IL-1b, IL-2, IL-4, bFGF, myeloblastin, and fibronectin.

45. An oligonucleotide as claimed in claim 1, wherein the oligonucleotide is directed against a viral target.

46. An oligonucleotide as claimed in claim 45, wherein the viral target is selected from HIV, HSV-1, HSV-2, influenza, VSV, hepatitis B, and papilloma virus.

47. An oligonucleotide as claimed in claim 1, wherein the oligonucleotide is directed against a target selected from integrins and cell-cell adhesion receptors.

48. An oligonucleotide as claimed in claim 47, wherein the oligonucleotide is directed against a target selected from VLA-4, VLA-2, ICAM or ELAM.

49. A process for the preparation of an oligonucleotide as claimed in claim 1, which comprises chemical synthesis on a solid support.

50. A process for the preparation of a pharmaceutical, which comprises mixing at least one oligonucleotide as claimed in claim 1 with a physiologically acceptable excipient and, if appropriate, suitable additives.

51. A process for the preparation of a pharmaceutical as claimed in claim 50, wherein the physiologically acceptable excipient is selected from lactose, corn starch, tallow, stearic acid, water, a polyol, sucrose, an inverted sugar, glucose, an alcohol, glycerol, a vegetable oil, a hardened oil, a wax, a fat, and a semiliquid polyol.

52. A process for the preparation of a pharmaceutical as claimed in claim 50, wherein the pharmaceutical further comprises one or more of a preservative, a solvent, a stabilizer, a wetting agent, an emulsifier, a sweetener, a colorant, a flavoring, a salt, a buffer, a coating agent, and an antioxidant.

53. A method of detecting a nucleic acid in a biological sample comprising:

(a) contacting said biological sample with a modified oligonucleotide as claimed in claim 1; and (b) detecting the presence or absence of a nucleic acid in the sample.

54. A method as claimed in claim 53, wherein said oligonucleotide contains 2–10 modified non-terminal pyrimidine nucleosides.

55. A method as claimed in claim 53, wherein one or more groups of at least one to four nucleotides which are linked together are not modified.

56. A method as claimed in claim 53, wherein said oligonucleotide has a length of approximately 6 to 100 nucleotides.

57. A method of preparing a pharmaceutical agent wherein an oligonucleotide of claim 1 is combined with a pharmaceutically acceptable excipient.

58. A method of preparing a diagnostic reagent wherein an oligonucleotide of claim 1 is combined with an acceptable carrier.

59. A method of inhibiting the expression of a specific target comprising the steps of:

(a) bringing an oligonucleotide of claim 1 in contact with the target; and (b) hybridizing the oligonucleotide with the target, wherein the oligonucleotide functions as an antisense oligonucleotide, a triple-helix forming oligonucleotide, an adaptamer, or a ribozyme.

60. A method of inhibiting the expression of a specific target comprising the steps of:

(a) bringing an oligonucleotide of claim 1 in contact with the target; and (b) hybridizing the oligonucleotide with the target.

61. A pharmaceutical composition comprising an oligonucleotide as claimed in claim 1, wherein the oligonucleotide may be used in the treatment of cancer.

62. A method of treating cancer comprising administering to a patient in need of treatment, a pharmaceutical composition as claimed in claim 61.

63. A pharmaceutical composition comprising an oligonucleotide as claimed in claim 1, wherein the oligonucleotide may be used in the treatment of a viral disease.

64. A method of treating a viral infection comprising administering to a patient in need of treatment, a pharmaceutical composition as claimed in claim 63.

65. A pharmaceutical composition comprising an oligonucleotide as claimed in claim 1, wherein the oligonucleotide may be used in the treatment of a disease affected by or involving integrins or cell-cell adhesion receptors.

66. A method of treating a disease affected by or involving integrins or cell-cell adhesion receptors comprising administering to a patient in need of treatment, a pharmaceutical composition as claimed in claim 65.

67. An oligonucleotide as claimed in claim 1, wherein the phosphorothioate modifications follow a pattern other than $((PS)_2-(PO)_2)_2-(PS)_2$.

* * * * *

UNITED STATES PATENT AND TRADEMARK OFFICE
CERTIFICATE OF CORRECTION

PATENT NO. : 6,348,312 B1 Page 1 of 1
DATED : February 19, 2002
INVENTOR(S) : Anuschirwan Peyman et al.

It is certified that error appears in the above-identified patent and that said Letters Patent is hereby corrected as shown below:

Title page,
Item [73], Assignee, "Hoescht" should read -- Hoechst --.
Item [57], ABSTRACT,
Line 3, "pharamaceutical" should read -- pharmaceutical --.

Column 31,
Lines 61-62, "a cytokins, a growth factors," should read -- a cytokin, a growth factor, --.

Signed and Sealed this

Ninth Day of September, 2003

JAMES E. ROGAN
*Director of the United States Patent and Trademark Office*

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

ACACCCAATT CTGAAAATGG                                              20

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

AGGTCCCTGT TCGGGCGCCA                                              20

(2) INFORMATION FOR SEQ ID NO:3:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GTCGACACCC AATTCTGAAA ATGGATAA                                     28

(2) INFORMATION FOR SEQ ID NO:4:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

GCTATGTCGA CACCCAATTC TGAAA                                        25

(2) INFORMATION FOR SEQ ID NO:5:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

```
TCGTCGCTGT CTCCGCTTCT TCTTCCTGCC A                                      31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CTGTCTCCGC TTCTTCTTCC TGCCATAGGA G                                      31

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCGGGGCTCC ATGGGGGTCG                                                   20

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CAGCTGCAAC CCAGC                                                        15

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGCTGCTGGA GCGGGGCACA C                                                 21

(2) INFORMATION FOR SEQ ID NO:10:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AACGTTGAGG GGCAT                                                        15
```

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CACGTTGAGG GGCAT                                                          15

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GTGCCGGGGT CTTCGGGC                                                       18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTGTCGGGGT CTCCGGGC                                                       18

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGAGAACATC ATGGTCGAAA G                                                   21

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCCGAGAACA TCATGGTCGA AG                                                  22

(2) INFORMATION FOR SEQ ID NO:16:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGGAAAGCC CGGCAAGGGG                                               20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CACCCGCCTT GGCCTCCCAC                                               20

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GGGACTCCGG CGCAGCGC                                                 18

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGCAAACTTT CTTTTCCTCC                                               20

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGGAAGGAGG AGGATGAGG                                                19

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GGCAGTCATC CAGCTTCGGA G                                              21

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTCTTCCATA GTTACTCA                                                  18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GATCAGGCGT GCCTCAAA                                                  18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TGAAGACGAC ATGATGTG                                                  18

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GGCTGCCATG GTCCC                                                     15

(2) INFORMATION FOR SEQ ID NO:26:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTGTAGTTTG ACGTGTGGG                                                    19

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GGCCCCTCCA GCCCCACATC CC                                                22

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GCAGTAAGCA TCCATATC                                                     18

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCCCCACCAC TTCCCCTCTC                                                   20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTCCCCCACC ACTTCCCCTC                                                   20

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GCTGGGAGCC ATAGCGAGG                                                    19

(2) INFORMATION FOR SEQ ID NO:32:

```
        (i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

ACTGCTGCCT CTTGTCTCAG G                                                    21

(2) INFORMATION FOR SEQ ID NO:33:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

CAATCAATGA CTTCAAGAGT TC                                                   22
```